United States Patent [19]
Lin

[11] Patent Number: 6,133,476
[45] Date of Patent: *Oct. 17, 2000

[54] PROCESS FOR PURIFICATION OF AROMATIC POLYCARBOXYLIC ACIDS

[76] Inventor: Tsong-Dar Vincent Lin, 5672 Sugar Hill Dr., Houston, Tex. 77056

[ * ] Notice: This patent issued on a continued prosecution application filed under 37 CFR 1.53(d), and is subject to the twenty year patent term provisions of 35 U.S.C. 154(a)(2).

[21] Appl. No.: 08/714,923

[22] Filed: Sep. 17, 1996

[51] Int. Cl.[7] .................................................. C07C 51/43
[52] U.S. Cl. ............................................................. 562/486
[58] Field of Search ............................................. 562/486

[56] References Cited

U.S. PATENT DOCUMENTS

| | | |
|---|---|---|
| 2,811,548 | 10/1957 | Ham . |
| 2,829,160 | 4/1958 | Stehman . |
| 2,862,963 | 12/1958 | Hofheim . |
| 4,201,871 | 5/1980 | Tenouchi .................................. 562/486 |
| 5,183,933 | 2/1993 | Harper .................................... 562/414 |
| 5,344,969 | 9/1994 | Iwane ..................................... 562/486 |
| 5,565,609 | 10/1996 | Hirowatari ............................. 562/485 |

FOREIGN PATENT DOCUMENTS

| | | | |
|---|---|---|---|
| 551596 | 7/1993 | European Pat. Off. | ............... 562/486 |
| WO 92/21645 | 12/1992 | WIPO . | |

*Primary Examiner*—Robert Gerstl
*Attorney, Agent, or Firm*—Thomason, Moser & Patterson, LLP

[57] ABSTRACT

The present invention provides a process for purifying crude aromatic polycarboxylic acids having one or more condensed rings, wherein two or more carboxylic acid groups can be at any position of the aromatic ring or rings. The process uses solvents consisting of two families of organic compounds as major solvent: a monocyclic compound containing two hetero-atoms and alkylamine compound, and two families of co-solvent: water and alcohol, to separate impurities from the crude acids. The product purity from the instant invention can be achieved to a level that is significantly better than the current state of the art.

13 Claims, No Drawings

PROCESS FOR PURIFICATION OF AROMATIC POLYCARBOXYLIC ACIDS

BACKGROUND OF THE INVENTION

The purification process in the instant invention applies to aromatic polycarboxylic acids having one or more condensed aromatic rings with two or more carboxylic acid groups at any position of the aromatic ring or rings. Typical examples of one-ring polycarboxylic acids are terephthalic acid, isophthalic acid and trimellitic acid; two ring aromatic polycarboxylic acids, 2,6-naphthlene dicarboxylic acid, 2,7-naphthalene dicarboxylic acids; three ring aromatic polycarboxylic acids, 2,3,6-anthracene tricarboxylic acid, etc. The background of terephthalic acid purification process is discussed first because of its largest commercial production quantity and it is the most difficult to purify due to its low solubility in most solvents, high boiling point, and similarities in physical and chemical properties with impurities present. Those skilled in the art would recognize that most principles discussed below for terephthalic acid are also applicable to other aromatic polycarboxylic acids.

Terephthalic acid has been well established as a starting material for manufacture of polyester fibers, films, and molding resin. However, the presence of its major impurities: p-toluic acid, benzoic acid, or 4-carboxybenzaldehyde (4-CBA), even in minute amounts, will adversely affect the quality of the polyester product from polymerization of terephthalic acid with ethylene glycol (MEG) into polyethylene terephthalate (PET). The impurities, such as monoffinctional p-toluic acid and benzoic acid, act as polymerization terminators that slow down the polymerization rate and decrease the average molecular weight of the polymer. Some other impurities, such as 4-CBA, cause undesirable coloring of the polymer as a consequence of their thermal instability during polymerization.

The purity specification for technical-grade terephthalic acid is 98.5+ wt %. However this purity is not high enough to be used as raw material for polyester production. Before polymer-grade, or pure terephthalic acid (PTA), can be commercially produced in 1965, technical-grade terephthalic acid was mainly used to produce polymer-grade dimethyl terephthalate (DMT) for its easier purification from crystallization and distillation. Either DMT or PTA is reacted with MEG to form bis(2-hydroxyethyl) terephthalate (BHET) which is condensation-polymerized to PET.

Polymer-grade terephthalic acid, i.e. PTA, must conform to many specifications to be suitable for the production of polyester fibers, films, and molding resin. Although no industry standards have been established officially, most polymer-grade terephthalic acids have maximum 25 ppm of residual 4-CBA and 150 ppm of p-toluic acid. Residual benzoic acid is generally low and not specified. However, significant amount of benzoic acid may still be present in some polymer grade terephthalic acids.

Currently, almost all technical-grade terephthalic acid is produced by catalytic liquid-phase air oxidation of para-xylene. This and other similar reactions producing crude aromatic polycarboxylic acids are referred to from time to time as oxidation reaction or oxidation reactions in this patent. Mid-Century process is the most widely adopted process which uses acetic acid as a solvent to assist slurry mixing and circulation; heavy metals, e.g., cobalt and manganese, as catalysts; and a bromine-containing compound as promoter. Reaction conditions are generally in the range of 175–230° C. and 1500–3000 kPa. A variant of the process uses acetaldehyde as oxidation promoter that runs at 120–175° C. and 700–1400 kPa. Some currently obsolete commercial processes are:

$HNO_3$ oxidation of para-xylene(PX). The process was used by du Pont in the U.S. and ICI in the United Kingdom.

Henkel I and II processes that rearrange benzoic acid or phthalic anhydride into terephthalic acid using naphthalene or toluene as starting material. These processes were used by Teijin, Kawasaki, and Mitsubishi in Japan.

Compared to DMT, advantages of polymer-grade terephthalic acid as a feedstock for PET are its lower cost, no methanol as by-product, lower investment and energy costs, higher unit productivity, and purer polymer because less catalyst is needed for the polymerization process. These factors, together with competitive marketing pressures, have induced a number of companies into developing processes that produce polymer-grade terephthalic acid since 1965. The success in the removal of impurities from technical-grade terephthalic acid has made polymer-grade terephthalic acid as a major and often the preferred feedstock for PET.

To produce polymer-grade terephthalic acid, separate purification processes have been developed to remove 4-CBA, p-toluic acid, and benzoic acid. The PTA process is separated into two sections: oxidation reaction section and purification section. The oxidation reaction section is for the production of technical grade or crude terephthalic acid (CTA) which is then introduced to purification section for removal of impurities. As discussed above, CTA production is generally produced by a liquid phase oxidation process. Terephthalic acid is also present as a major constituent in intermediate streams of the DMT production processes.

With slight variations, the prior art teaches that the purification section removes 4-CBA from terephthalic acid by chemically converting 4-CBA into p-toluic acid through hydrogenation reaction using charcoal supported noble metals, such as platinum, palladium, and so on, as the catalysts. P-toluic acid (converted from 4-CBA or existing in terephthalic acid as contaminant) is generally removed by recrystallizing terephthalic acid from water at elevated temperatures and pressures. An alternative is continuing further oxidation of 4-CBA to terephthalic acid.

However, this type of purification method, either by hydrogenation or oxidation, although efficient, can only handle relatively small amount of 4-CBA present in CTA initially. To meet the final polymer-grade PTA product specification, 4-CBA, the principal impurity present in CTA, is generally limited to less than 1.0 wt %, preferably less than 0.5 wt %, to avoid overloading the purification section of the process.

To achieve this purpose of reducing the amount of impurities introduced into the purification section, either the equipment has been modified to run at higher severity, or additional processing steps are added after the oxidation reaction step, such as a secondary oxidation step or reslurrying CTA in fresh acetic acid. Because higher severity increases the combustion rate of para-xylene, the CTA feedstock, and acetic acid, the preferred solvent, to CO and $CO_2$, the overall yield of the desired product and production efficiency are both reduced. Using acetic acid as solvent and operating under severe condition require reactors and some other parts of the process to use expensive corrosion resistant material, such as titanium. This requirement increases initial capital investment significantly. Adding more processing steps likewise requires higher capital investments. Therefore, most prior arts teach the use of a relatively cumbersome purification procedure and high-cost equipment to remove as little as 0.5 wt % of impurities from terephthalic acid.

In searching for alternative methods to produce polymer-grade terephthalic acid, earlier patents disclosed that terephthalic acid could be purified by crystallization in organic solvents. A partial list of those solvents is given below 1. N,N-dimethylacetamide, or N,N-diemthylformamide, or their mixtures with water or methanol (U.S. Pat. No. 2,811,548);
2. Pyridine with isopropylamine and others, recrystallizing in ethylene glycol, and acidifying in acid water (U.S. Pat. No. 2,829,160);
3. N-formyl morpholine, or N-formnyl piperidine (U.S. Pat. No. 2,849,483);
4. Ammonia with methanol and acetone (U.S. Pat. No. 2,862,963).

These disclosed organic solvents, however, have several disadvantages. They are unable to produce the required high purity terephthalic acid. They are either unstable themselves or tend to form additional products with terephthalic acid. It is also difficult to separate the residual solvent included in the crystals of the product.

On the other hand, the thermally more stable and chemically much less reactive solvents such as acetic acid, acetic anhydride (U.S. Pat. No. 3,574,727) and water, suffer from low solubility of terephthalic acid and lack of selectivity between terephthalic acid and 4-CBA. With this type of solvents, expensive hydrogenation process is required to convert 4-CBA into p-toluic acid most of which can be later removed by recrystallization in water (U.S. Pat. No. 3,584,039).

The manufacturing processes of isophthalic and phthalic acid that have the two carboxylic acids located at meta and ortho positions are similar to the manufacturing process of terephthalic acid. Liquid-phase oxidation production facilities often can be used interchangeably between terephthalic acid and isophthalic acid. Phthalic acid produced by this liquid process has significantly higher yields than those from vapor-phase oxidation processes with higher capital costs.

The manufacturing process of benzenetricarboxylic acid is also similar to the terephthalic acid process. Trimellitic acid is produced commercially in large volume in the U.S. mainly by liquid-phase air oxidation of pseudocumene. It is dehydrated to trimellitic anhydride, a preferred form commercially. Trimellitate esters have many superior properties than phthalic acid esters in certain applications. For example, trimellitate esters are used as plasticizers for poly-vinyl chloride, especially if permanency is required, e.g., in high temperature wire insulation. Other important uses of trimellitate esters are in alkyd resins, amide-imide polymers, and epoxy curing.

The manufacturing process of aromatic polycarboxylic acids with two condensed rings, such as naphthalene dicarboxylic acids (NDA), is also similar to terephthalic acid process. 2,6- or 2,7-NDA can be produced by the oxidation of 2,6- or 2,7-dialkyl naphthalene respectively with air or oxygen enriched air, in the presence of cobalt, manganese, and bromine. Relative to PTA, 2,6-NDA imparts greater structure stability to the resulting polymers at the same molecular level. Since the crude NDA also contains impurities, such as trimellitic acid, bromo-2,6-NDA, 2-naphthoic acid, 2-formyl-6-naphthoic acid, a similar purification process is required.

To improve NDA purity, a number of Japanese patents described the methods of dissolving the crude NDA in an aqueous solution of alkali, then subjecting the solution to such treatment as oxidation, hydrogenation, decoloring by adsorption, and so on, and followed by acidifying the resulting solution, thereby obtaining the purified NDA (JP-A48-68554, JP-B-52-20993, JP-A-50-105639, and JP-A-50-16024). However, the above methods suffer several drawbacks, that large amounts of acid and alkali have to be used, that an inorganic salt is produced, and that waste water is discharged in large quantities.

Organic solvents were also disclosed for purifying crude NDA as described by JPA-62-230747. An organic solvent selected from N,N-dimethylformamide (DMF), N,N-dimethylacetamide, and dimethyl sulfoxide (DMSO), treating the solution with active carbon, and then recrystallizing the purified NDA. However, the solubility of NDA in DMF or DMSO is low, so large quantity of solvent has to be used. Furthermore, it was found, in a higher NDA recovery mode, almost no improvement in color was achieved in the purified NDA product. Toxicity of the solvents is also a major concern. In addition, they are difficult to recover due to their high boiling points (U.S. Pat. No. 5,344,969).

An aqueous solution of alkylamines such as dimethylamine, was used to dissolve crude NDA and the purified NDA was precipitated by removing dimethylamine from the solution by distillation (JP-A-50-142542). However, a large portion of water in the aqueous solution is lost along with the amine because the amine evaporates as an azeotropic mixture with water. NDA recovery by the method is low because complete removal of the amine from the aqueous solution is extremely difficult.

Another alternative was to use alkylamines and alcohols to dissolve crude NDA. The purity and color of NDA were improved by precipitating NDA solids from the solution by one of the following precipitation method (U.S. Pat. No. 5,344,969):

1. Cooling to precipitate an amine salt of NDA, and the amine is then recovered from the amine salt by heating, thereby to obtain NDA having high purity.
2. Cooling to precipitate an amine salt of NDA, and the amine is then treated with an acid, thereby to obtain NDA having high purity.
3. Adding an acid to the solution, thereby to obtain NDA having high purity.

The prior arts of purification by crystallization used either a pure organic solvent or a mixture of solvents at constant composition to dissolve crude aromatic polycarboxylic acids at high temperature. The solution was then cooled to precipitate solids and leave impurities in the solution to purify the acids. These processes mainly took advantage of differences in solubility at different temperature to dissolve the crude acids and precipitate the solids. Since the solubility of the crude acids in these solvents is generally insignificant around room temperature (25° C.), the processes were focused to find a solvent or a solvent mixture having high solubility for the crude acids at high temperature. The solvent of course has to meet additional requirements, such as non-reactive with the crude acids, easy to be recovered, and extremely low amount of residual solvent to be remained in the purified product, etc.

SUMMARY OF THE INVENTION

It was unexpectedly found in this invention that the solubilities of the crude acids and impurities vary significantly with the composition of a mixture of solvents at both of low and high temperature. To dissolve crude acids, the higher of the solubility is the better. To precipitate solids, the lower of the solubility is the better. It was found, in some cases at room temperature, that the solubility of a solvent mixture at a composition can be as high as around 60 wt % that is a level difficult to be reached by processes in prior arts. By simply changing the composition alone, the solubility can be reduced to insignificant level. In the instant invention, the process takes the advantage of differences in solubility at different composition, in addition to temperature, to improve product purity and reduce the costs of dissolution and precipitation.

The present invention provides a process for purifying crude aromatic polycarboxylic acids having one or more condensed rings, wherein two or more carboxylic acid groups can be at any position of the aromatic ring or rings. The process comprises: (1) dissolving the crude aromatic polycarboxylic acid in a mixed solvent selected from the group consisting of N,X-monocyclic compound, alkylamine compound, water, alcohol, acid, or other co-solvent; (2) optionally pre-treating the solution with filtration, or activated carbon or other proper absorbents; (3a) crystallizing by changing the solvent composition or temperature and then dissolving the crystallized salt into an acid solvent, or (3b) crystallizing by changing the solvent composition or temperature and then heating the crystallized salt to decompose the salt, or (3c) crystallizing by direct adding an acid solvent to solution; (4) filtering and optionally washing with a mixed solvent to obtain a purified crystalline product that meets or exceeds the current industrial standard at lower capital and operating costs; (5) before drying, optionally re-dissolving the purified crystalline product into a mixed solvent to re-crystallize by flashing or evaporation, with or without cooling, to further improve product qualities; and (6) drying.

These steps may be carried out with or without a purge of an inert or non-oxidizing gas. Some of these steps may be repeated to further improve product purity.

The instant invention has the following major advantages:
1. Purification cost by crystallization is lower than the cost by chemical reactions. The capital and operation costs for product purification are significantly lower than the current commercial purification processes.
2. The product purity obtained from this invention can meet and exceed the current industrial standard. It is even possible to reach to the ultra-pure level that the impurities almost cannot be detected by the current HPLC measuring method. This may allow manufacturing of polymers that are not possible to obtain with the current levels of aromatic polycarboxylic acid purity.
3. This new approach can process crude aromatic polycarboxylic acids having much higher impurity content. This capability introduces several synergistic effects that include relaxing requirements in oxidation reaction section to reduce operation and capital investment costs, allowing to process the crude acids from intermediate streams in esterification processes, such as DMT or NDC esters, recovering aromatic polycarboxylic acids present as byproduct and/or impurity in some process streams, or further purifying pure aromatic polycarboxylic acids to ultra pure level.

DETAILED DESCRIPTION OF THE INVENTION

Crude Aromatic Polycarboxylic Acids

The aromatic polycarboxylic acids that may be purified in accordance with the present invention are those having one or more condensed rings, wherein two or more carboxylic acid groups can be at any position of the aromatic ring or rings. The one-ring aromatic dicarboxylic acids include terephthalic acid, isophthalic acid, and orthophthalic acid. Other one-ring aromatic polycarboxylic acids include trimellitic acid, hemimellitic acid, trimesic acid, pyromellitic acid, mellitic acid, etc. The two-ring aromatic polycarboxylic acids include 2,6-naphthalene dicarboxylic acid, 2,7-naphthalene dicarboxylic acid, 1,7-naphthalene dicarboxylic acid, and 1,8-naphthalene dicarboxylic acid. Other two-ring aromatic polycarboxylic acids include 2,3,6-naphthalene tricarboxylic acid, 1,4,5,8-naphthalene tetracarboxylic acid, 2,3,6,7-naphthalene tetracarboxylic acid, etc. The three-condensing ring aromatic polycarboxylic acids include 2,6-anthracene dicarboxylic acid, 2,7-anthracene dicarboxylic acid, 2,8-anthracene dicarboxylic acid, 2,9-anthracene dicarboxylic acid, or 1,9-anthracene dicarboxylic acid. Other three-ring aromatic polycarboxylic acids include 2,3,6-anthracene tricarboxylic acid, 1,4,5,8-anthracene tetracarboxylic acid, 2,3,6,7-anthracene tetracarboxylic acid, etc.

Most crude aromatic dicarboxylic acids are obtained by oxidation processes of poly-substituted aromatic compounds with air or oxygen enriched air. These processes have been described by numerous patents and publications. For example, the oxidation of xylene isomers produces one-ring aromatic dicarboxylic acids; the oxidation of the di-substituted naphthalenes, such as dimethylnaphthalenes, produces aromatic dicarboxylic acids with two condensed rings; and the oxidation of the substituted anthracenes produces three-ring aromatic dicarboxylic acids. These oxidation processes are generally carried out in a solvent, e.g., a lower aliphatic monocarboxylic acid or water, in the presence of a catalyst, i.e., one comprising heavy metals such as cobalt, manganese, or their mixture, and in the presence of a promoter such as bromine. Acetic acid is the most popular lower aliphatic monocarboxylic acid that used as solvent for the oxidation process.

The oxidation reaction is conducted usually at a temperature range of from about 170° C. to about 300° C., depending on the aromatic feed to the oxidation reactor, with the oxygen partial pressure in the gas phase being preferably from 0.2 to 20 $Kg/cm^2$ in terms of absolute pressure. After completion of the oxidation reaction, the reaction mixture is cooled to around room temperature and the precipitated crude aromatic polycarboxylic acid is recovered.

The other possible source of crude aromatic polycarboxylic acid is from the intermediate stream product in an aromatic polycarboxylic ester production process. For example, crude terephthalic acid can be recovered by filtration from the oxidizer effluent during the production of DMT; or crude 2,6-NDA can be recovered by filtration from the oxidizer effluent during the production of dimethyl-2,6-naphthalene dicarboxylate (NDC). The impurity content for terephthalic acid obtained from DMT process may be as high as 30 wt %. This is significantly higher than 0.5–1.0 wt % levels typically found in the catalytic liquid-phase air oxidation processes. Consequently, it will cause overloading problem in prior art purification processes by either oxidation or hydrogenation as discussed previously. However, the present invention is capable to purify such a kind of intermediate product to their polymer-grade specifications.

Crude aromatic polycarboxylic acid can also be produced from $HNO_3$ oxidation of PX, or from Henkel I and II processes that use naphthalene, toluene, benzoic acid or phthalic anhydride as starting or intermediate material. This instant invention is also capable of purifying such materials. The major impurities in the more common crude aromatic polycarboxylic acids (CAPA) are listed below:

| | Process | Impurities |
|---|---|---|
| Terephthalic acid | Oxidation | 4-CBA, p-toluic acid, benzoic acid |
| Isophthalic acid | Oxidation | 3-CBA, m-toluic acid, benzoic acid |
| Orthophthalic acid | Oxidation | 2-CBA, o-toluic acid, benzoic acid |
| 2,6-NDA | Oxidation | Trimellitic acid, bromo-2,6-NDA, 2-naphthoic acid, 2-formyl-6-naphthoic acid |
| Terephthalic acid | Esterification | 4-CBA, p-toluic acid, benzoic acid, monomethyl terephthalate, dimethyl terephthalic acid, methyl p-toluate, dimethyl terephthalate, methylbenzoate |
| 2,6-NDA | Esterification | Trimellitic acid, bromo-2,6-NDA, 2-naphthoic acid, 2-formyl-6-naphthoic acid, 2,6-NDC, 2-formyl-6-naphthoic acid, esters of trimellitic acid, etc. |

In addition to these listed impurities, some other trace compounds may be present in various CAPA production processes, such as ashes, metals, halides, color substances, p-cresol, 4-hydroxylmethyl benzoic acid, 4-formyl-benzoic acid, 4-hydroxymethyl-benzaldehyde, methyl acetate, p-tolualdehyde, bromo-2,6-naphthalene dicarboxylic acid, 2-formyl-6-napththoic acid, etc. Organic acid or inorganic acid, such as acetic acid, carried over from the oxidation reaction section may also be present.

Solvents

The following lists the solvents that are used in this invention. These solvents used may include a single solvent, a mixture, or an admixture of solvents that can be miscible or immiscible. The solvents are categorized into major solvents, co-solvents, and acid solvents. A mixed solvent is a combination of a major solvent, a co-solvent, and an acid solvent in any proportions. Detailed combinations are described at the appropriate sections of the specifications.

Major Solvents

Major solvents play the major role in dissolving aromatic polycarboxylic acids and impurities by forming weakly bonded complexes with the acids. Two solvent groups are used in this invention as major solvents: N,X-monocyclic compounds and alkylamine compounds. A major solvent also includes a mixture of N,X-monocyclic compound and alkylamine compound in any proportion.

N,X-Monocyclic Compound

An N,X-monocyclic compound in this invention is a mono-heterocyclic compound containing 3 to 8 atoms in the ring with a nitrogen(N) and an hetero-atom(X), such as oxygen, sulfur, or another nitrogen, as the hetero-atoms. The nitrogen atom may have three or five valences. The compound includes all combinations of hetero-atom and carbon-atom at different positions in the ring, and their saturated and unsaturated compounds with one or more hydrogen atoms that may be substituted by an alkyl, aryl, or acyl group. The N,X-monocyclic compound also includes the ammonium salts derived from such compounds.

The N,X-monocyclic compound includes parent compounds, i.e. a given number of atoms in a ring including all of the unsaturated and saturated with hetero-atom at all possible ring positions, such as oxazocines, oxazepines, oxazines, oxazoles, isoxazoles, oxadiazetes, oxazirines, thiozocines, thiazepines, thiazines, thiazoles, isothiazoles, thiazetes, thiazirines, diazocines, diazepines, pyrazines, pyridazines, pyrimidines, imidazoles, pyrazoles, diazetes, diazirines, etc. If a compound is in solid or gaseous form under normal condition, then its aqueous solution from 0.0001 wt % to saturation will be used.

The N,X-monocyclic compound can be used either alone or as a mixture of two or more thereof in any proportion. The preferred N,X-monocyclic compound for this invention is a saturated oxazine or mixtures of said oxazines. The commonly used or adopted name of the saturated oxazine is morpholine, CAS Registry Number 110-91-8. A morpholine compound in this invention means morpholine, substituted morpholines, morpholine derivatives, and mixtures thereof. Typical examples of a morpholine compound are morpholine, N-methylmorpholine, N-ethylmorpholine, N-propylmorpholine, N-isopropylmorpholine, N-methylmorpholine oxide, N-phenylmorpholine, 4-morpholinepropionitrile, 1-morpholine-1-cyclohexene, etc.

Other examples are piperazine, N-methylpiperazine, 2-methylpiperazine, N,N-dimethylpiperazine, etc. Two other compounds are also included as members of this group: 1,4-diazabicyclo[2.2.2]octane (CAS Registry Number 280-57-9), 1,8-diazabicyclo [5.4.0]undec-7-ene (CAS Registry Number 6674-22-2). 1,4-diazabicyclo[2.2.2]octane is also a preferred compound.

Alkylamine Compound

An alkylamine compound in this invention includes aliphatic amine; alicyclic amines; ammonium salts derived from these aliphatic and alicyclic amines.

Aliphatic amines include methylamine, dimethylaamine, trimethylamine, ethylamine, diethylamine, triethylamine, n-propyamine, di-n-propylamine, tri-n-propylamine, isopropylamine, diisopropylamine, triisopropylamine, cyclohexylamine, and $C_4$ to $C_8$ aliphthalic amines. Other examples of suitable amines are ethylenediamine, N-methylethyleneamine, N,N-dimethylethylenediamine, N,N'-dimethylethylenediamine, N,N,N'-trimethylethylenediamine, N,N,N',N'-tetramethylethylenediamine, 1,2-diaminopropane, 1,3-diaminopropane, N-methyl-1,2-diaminopropane, N-methyl-1,3-diaminopropane, N,N-dimethyl-1,2-diaminopropane, N,N-dimethyl-1,3-diaminopropane, N,N,N'-trimethyl-1,2-diaminopropane, N,N,N'-trimethyl-1,3-diaminopropane, N,N,N',N'-tetramethyl-1,2-diaminopropane, N,N,N',N'-tetramethyl-1,3-diaminopropane, monoethanolamine, diethanolamine, triethanolamine, and glycine.

Alicyclic amines include pyrrolidine, 1-methylpyrrolidine, piperidine, N-methylpiperidine, hexamethyleneimine, and N-methyl hexamethyleneimine. If a compound is in solid or gaseous form under normal condition, then its aqueous solution from 0.000 wt % to saturation will be used. Among these alkylamine compounds, aliphatic amines having up to 15 carbon atoms are preferred. Triethylamine and triethanolamine are the most preferred alkylamine compounds. Again, these alkylamine compounds may be used either alone or as a mixture of two or more thereof in any proportion.

Co-Solvent

Two classes of co-solvents are used in this invention: water and alcohol. The co-solvent also includes mixtures of water and alcohol in any proportion. Oxygen-containing solvents may be used together with water and/or alcohol to further enhance selectivity for product recovery or impurity removal. Major solvents form weakly bonded complexes with crude aromatic polycarboxylic acids, and the amount of complex dissolved may vary depending on the composition of the co-solvent and the temperature of the solution. In this invention, co-solvent composition is one of the important controlling factors to enhance the selectivity for product recovery and/or impurity removal. The composition is the concentration of components in a mixture. Co-solvents may also be used alone or with an acid solvent and/or major solvent to wash out residual impurities captured in the inclusion of the precipitated crystals.

Water

Water is the most inexpensive, abundant, and nontoxic solvent. It normally does not react with crude aromatic polycarboxylic acids and their impurities under the operating conditions in this invention. Using water as co-solvent not only enhances the selectivity for product recovery, impurity removal, or both, but also reduces the overall cost of solvent used to dissolve crude aromatic polycarboxylic acids.

Alcohol

An alcohol, as a co-solvent, is selected from the groups consisting of aliphatic monohydric alcohols such as methanol, ethanol, n-propanol, isopropanol, n-butyl alcohol, isobutyl alcohol, sec-butyl alcohol, tert-butyl alcohol, n-amyl alcohol, isoamyl alcohol, sec-amyl alcohol, tert-amly alcohol, neopentyl alcohol, hexyl alcohol, heptyl alcohol, octyl alcohol, nonyl alcohol, and decyl alcohol; alicyclic monohydric alcohols such as cyclopentyl alcohol and cyclohexyl alcohol; aliphatic straight-chain diols such as ethylene glycol, diethylene glycol, glycerol, 1,2-propylene glycol, and 1,3-propylene glycol; alicyclic diols such as 1,2-cyclopentanediol, 1,3-cyclopentanediol, 1,2-cyclohexanediol, 1,3 cyclohexanediol, 1,4-cyclohexanediol; and aliphatic polyols such as glycerol and pentaerythritol. Aliphatic monohydric alcohols having 3 or less carbon atoms and diols having 3 or less carbon atoms, are preferred. Alcohols can be used either alone or as a mixture of two or more thereof in any proportion.

Oxygen-containing Solvents

In addition to water and alcohol, other oxygen-containing solvents may also be used with water, alcohol, or a water and alcohol mixture to further enhance the selectivity of product recovery or impurities removal. The oxygen-containing solvents include ketones, ethers, aldehydes, glycols, and alicyclic compounds such as furan, dihydrofuran, tetrahydrofuran, tetrahydropyran, 2-methyl cyclopentanone, cyclopentanone, cyclohexanone, cyclohexanol, 2-methyl tetrahydrofuran, 3-methyl tetrahydrofuran, gamma-butyrolactone, gamma-valerolactone, etc. Again, these oxygen-containing solvents may be used alone or as a mixture of two or more thereof in any proportion. Co-solvents also include mixtures of water, alcohol, and oxygen-containing solvent in any proportion.

Acid Solvent

An acid solvent includes aliphatic carboxylic acids such as formic acid, acetic acid, propionic acid, butyric acid, glycolic acid, lactic acid, malic acid, tartaric acid, mesotartaric acid, citric acid, monochloroacetic acid, monobromoacetic acid, trifluoroacetic acid, and trichloroacetic acid; and inorganic acids such as nitric acid, hydrochloric acid, hydrogen bromide, hydrogen iodide, sulfuric acid, phosphoric acid, and perchloric acid. If an acid is in solid or gaseous form under normal operating conditions, its aqueous solution from 0.000 wt % to saturation is used in this invention.

These acids may be used either alone or as a mixture of two or more thereof in any proportion provided they are chemically compatible. Those who are skilled in the art would recognize and appreciate that, for example, concentrated sulfuric acid should not be used with hydrogen iodide. The acid may be used as is or in the form of an aqueous solution. An aliphatic carboxylic acid having up to 15 carbon atoms, such as acetic acid, is preferred. The amount of an acid used is in the amount from about 0.01 to 100 times, preferably from about 0.2 to 10 times, in molar ratio, to the amount of crude acid present in the solution. The acid solvent also includes a mixture of the acid with a co-solvent, in a range from about 0 wt % to about 100 wt %, preferably in a ratio from about 50 wt % to about 99 wt %.

Mixed Solvent

A mixed solvent is a mixture of a major solvent and a co-solvent, a co-solvent and an acid solvent, a major solvent and an acid solvent, or a major solvent, a co-solvent and an acid solvent, and other combinations that contain oxygen-containing solvents. The mixed solvent comprises a major solvent from 0.1 wt % to 99.9 wt %, a co-solvent from 0.1 wt % to 99.9 wt %, an acid solvent from 0 wt % to 99.9 wt %, and an oxygen-containing compound from 0 wt % to about 85 wt %.

The proportion of the N,X-monocyclic compound to water or alcohol is from 1:1000 to 1000:1 by weight, preferably from about 25:75 to about 95:5 by weight. The proportion of the alkylamine compound to water or alcohol in the mixed solvent is from 1:1000 to 1000:1 by weight, preferably from about 25:75 to 95:5 by weight.

The exact amount of the major or mixed solvent to be used in this invented process is not specifically limited as long as it is sufficient to dissolve the crude aromatic polycarboxylic acid to minimize losses of CAPA. The amount usually varies depending on the composition and concentration of water or alcohol present in the N,X-monocyclic compound or alkylamine compound, and the temperature at which the crude aromatic polycarboxylic acid is dissolved. The amount of a major solvent or a mixed solvent is used in the range of from about 0.1 to 100 times by weight, preferably from about 1 to 50 times by weight, to the amount of the crude aromatic polycarboxylic acid. If the amount of solvent used is below the lower limit specified above, purification effect may be insufficient. If the amount exceeds the upper limit specified above, while technically feasible and included in this invention, the process becomes less economical.

As a crude aromatic polycarboxylic acid is dissolved in a major solvent, a major solvent and a co-solvent, or a mixed solvent, the mixture is called a solution. After aromatic polycarboxylic acid is precipitated from the solution, the remaining solution is called a mother liquor.

Most major solvents do not react with oxygen in air under the operating conditions of this invention, but some may slightly do and cause gradual change of solvent color. Under this circumstance, the process will be preferably operated under low oxygen environment or non-oxidizing atmosphere in a closed system and/or by purging with a non-oxidizing or inert gas or other suitable methods. Examples of such non-oxidizing or inert gases are $N_2$, $CO_2$, CO, Ar, He, $H_2$, etc., and $N_2$ and $CO_2$ are preferred.

In most cases, the co-solvent is used to increase crude aromatic polycarboxylic acid solubility. However, in other cases, the co-solvent is used to decrease the solubility of the acid to enhance product recovery. For instance, pure N-methyl morpholine oxide has about 15% solubility for terephthalic acid at room temperature. This solubility is too high for product recovery. However, adding suitable amount of water to the solution will reduce the solubility and enhance product recovery.

The mixed solvent may be miscible or immiscible mixture of its components. Therefore, the mixed solvent may be in a single phase or multiple phases. In the case of multiple liquid phases, the solubilities of crude aromatic carboxylic acids and impurities in different liquid phase may be different. A proper choice of solvent in different phase allows us to take advantage of liquid-liquid extraction method to separate the impurities.

Solution Pretreatment

The key to these purification processes is to precipitate pure aromatic polycarboxylic acids from solutions while keeping as much impurities in the solution as possible. However, crude aromatic polycarboxylic acids may contain insolubles, color substances, or impurities that can be easily separated by a pretreatment of the solution. The following lists the optional pretreatment methods that can be used individually or in any combination to remove such substances.

Crude aromatic polycarboxylic acid may contain insoluble impurities that can be separated by using any suitable method, such as filtration, centrifugation, sedimentation, magnetic separation, evaporation, and others.

The solution may be treated with an activated carbon or other suitable adsorbents by:

(1) a batch-wise method in which a predetermined amount of activated carbon or other adsorbent is added to the solution, and the resulting mixture is stirred, with or without heating, and then filtered; Or (2) a counter current or concurrent continuous method in which the solution is passed through a column packed with activated carbon or other adsorbents.

Using one or more stages of liquid-liquid extraction to remove impurities by choosing solvents that are not immiscible.

Purification Processes

A purification process used in this invention means one or a combination of the following five processes. The choice depends on the aromatic polycarboxylic acid to be purified, the solvent selected, and the operating conditions. Details are set forth throughout the specifications. The processes can be used for one or more times. First, a crude aromatic polycarboxylic acid having one, two, three or more condensed rings is dissolved in a selected solvent or solvent mixture. Depending on the crude aromatic polycarboxylic acid to be purified, the solvent or solvent mixture may contain a particular group of major solvent, co-solvent, or mixtures thereof. Whether specifically described or not, this purification process can be carried out with or without a purge of a non-oxidizing or inert gas in all phases. Typical gases are $N_2$, $CO_2$, CO, Ar, He, $H_2$, and others.

Following this dissolution step is a step of purification process selected from the five processed described below. While the basic theories of this invention are also described and they are believed to be true, they are used only to illustrate and demonstrate the invention. In no way are these theories intended to limit the scopes or inventiveness of this invention.

Process 1.
(a) Changing the composition of the solvent used to dissolve the crude aromatic polycarboxylic acid by removing lower-boiling components in the mixed solvent by flashing under reduced process pressure, by evaporating at constant or variant temperatures, by distillation, or by adding more co-solvent, to precipitate the solid formed between aromatic polycarboxylic acid and the major solvent. In the case of evaporation or flashing, the solid is precipitated mainly due to the change of solvent composition and the reduction of solvent quantity.
(b) Separating the precipitated solid followed by treating the separated solid with an acid solvent to obtain a purified aromatic polycarboxylic acid.

Process 2.
(a) The same process as 1 (a) is used to precipitate a solid.
(b) Separating the precipitated solid followed by heating the separated solid to a higher temperature, with or without purging with a non-oxidizing or inert gas such as $N_2$, $CO_2$, CO, He, Ar, $H_2$, and others, to decompose the solid to obtain a purified aromatic polycarboxylic acid.

Process 3.
(a) A crude aromatic polycarboxylic acid is dissolved in a solvent at elevated temperature. The solution is cooled to a lower temperature to precipitate the solid formed between aromatic polycarboxylic acid and the major solvent. The solid is precipitated mainly due to the change of temperature in solution.
(b) The solid is separated and then treated with an acid solvent to obtain a purified aromatic polycarboxylic acid.

Process 4.
(a) The same process as 3 (a) is used to precipitate a solid.
(b) The solid obtained is separated and then heated to a higher temperature, with or without purging with a non-oxidizing or inert gas, such as $N_2$, $CO_2$, CO, He, Ar, $H_2$, and others, to decompose the solid to obtain a purified aromatic polycarboxylic acid.

Process 5.
An acid solvent is added to the solution containing the crude aromatic polycarboxylic acid, at constant or variant temperature, to precipitate a purified aromatic carboxylic acid from the solution. The purified aromatic polycarboxylic acid solid is precipitated mainly due to the change of complex structure. The acid component substitutes the aromatic polycarboxylic acid and form a new complex with the major solvent.

In Process 1 and Process 2, the control and change of the solvent composition depend on the major solvent and co-solvent selected for a particular aromatic polycarboxylic acid and the desired process conditions. Absolute and relative solubilities of the aromatic polycarboxylic acid to be purified and the impurities present are of paramount importance. For instance, at lower temperatures such as room temperature, the solubilities of aromatic polycarboxylic acids are generally low in most major solvents or co-solvents. However, at the lower temperatures, it was unexpectedly discovered that the solubilities of aromatic polycarboxylic acids vary significantly with the composition of the mixture. Most solubilities are negligible in a pure major solvent, increase with the addition of a co-solvent, reach to a maximum, and then gradually decrease to negligible again in a pure co-solvent composition. However, some major solvents were found to have significant solubilities for aromatic polycarboxylic acids at room temperature, and gradually decrease with increasing amounts of co-solvent in the compositions. This invention takes advantage of all these discovered surprising and unexpected differences in the purification process.

Impurity solubilities also vary with co-solvent compositions. Generally, their solubility patterns were found to be similar to, but in a significantly higher absolute level than, aromatic polycarboxylic acid solubilities in a range of compositions. Therefore, there exists an optimal way to control the solvent composition in order to achieve best product recovery and impurity removal.

Higher-boiling components may leave together with lower-boiling components in Process 1 and Process 2. The total amount of solvent removed from the mixed solvent is from about 0.1 to 100 wt % of its original amount presented in the mixed solvent, preferably from about 50 to 95 wt %. In the case of adding more co-solvent as part of the purification process, the added amount may change the final co-solvent composition from 0.01 to 99.9 wt %, preferably from about 20 to 75 wt %. The temperature of solution is from about −100 to 350° C., preferably 30 to 180° C.; the pressure is in a range of 1 mmHg (absolute) to 100 atmospheres (absolute), preferably about 20 mmHg (absolute) to 2.0 atmosphere.

In Process 3 and Process 4 above, a crude aromatic polycarboxylic acid is precipitated from solution by cooling. The dissolving temperature may be in the range from about −100 to about 350° C., preferably from about 80 to 170° C. The temperature may be cooled to the range from about −100 to 150° C., preferably from 25 to 100° C., more preferably from about 40 to 60° C.

In Process 5, an acid solvent is added to the solution to precipitate purified aromatic polycarboxylic acid while keeping most of impurities in solution. The amount of acid solvent used may be from 0.01 to 100 times, preferably, about 0.2 to 30 times, in molar ratio, to the number of moles of crude aromatic polycarboxylic acid present. The operating temperature may vary from about −100 to 350° C., preferably from about 25 to 180° C. This process may be used for 1 to 100 times, preferably, 1 to 3 times.

The solids precipitated by Process 1 and Process 3 are treated by adding a predetermined amount of an acid solvent to the solids. The resulting admixture is stirred at a temperature from about −100 to 350° C., preferably from about 25 to 180° C., for a period of about 0 to 10 hours, preferably from 0 to 2 hours. The purified aromatic polycarboxylic acid is recovered subsequently from the mixture. The amount of acid solvent used may be from about 0.01 to 100 times by mole, preferably, about 0.2 to 10 times by mole, to the amount of crude aromatic polycarboxylic acid. This process may be used for 1 to 100 times, preferably 1 to 3 times.

In Process 2 and Process 4, the exact temperature used to decompose the solids to obtain a purified aromatic polycarboxylic acid is not specifically limited as long as it is sufficient for the decomposition.

Filtration And Product Recovery

The solids obtained from one of the above five processes are filtered or by other suitable methods to remove the mother liquor from the solids. The mother liquor from the separation of solid in various stages of the above purification process containing impurities. The mother liquor can be re-used repeatedly for crystallization, without any particular treatment or, if required, after being subjected to purification. The mother liquor may be recycled or purified by any suitable method, such as distillation, filtration, centrifugation, sedimentation, evaporation, cooling, adding more solvent, etc., or any combination of the methods, to separate impurities. The recovered impurities can then be recycled totally or partially to the oxidation reaction section or removed from the process.

The filtered solids may be optionally subjected to post-treatment such as washing or other methods for further removal of impurities, solvents, or acid, as described in the following section, before drying. The solids are then dried by any suitable method known to those skilled in the art to remove any residual co-solvent or traced acid and major solvents from the solids.

With one or a combination of the above mentioned processes of this invention, purified aromatic polycarboxylic acids with high purity can be obtained from the crude aromatic polycarboxylic acids.

Post Treatment

All filtered solids obtained from the above methods can be optionally washed one or more times with a co-solvent, acid solvent, or mixed solvent to remove residual impurities from the solids. The temperature of the washing solvent can be between about 0° C. to about 150° C., preferably from about 25° C. to about 100° C. The amount of washing solvent used to the amount of aromatic polycarboxylic acid present is in the range from about 0.01 to about 100 times by molar ratio, preferably, from about 0.2 to about 10 times.

The particle sizes obtained from the above methods are generally finer, but more uniform, than those from the current PTA processes. As a result, the bulk density of the PTA produced by this invention may be different from those of current commercial products. If desirable, the bulk density of PTA produced by this instant invention can be adjusted by re-crystallization. This can be achieved by a number of means known to those skilled in the art. Only one example is given here. The PTA solids from this invention is dissolved in a co-solvent or acid solvent, such as water or acetic acid, at elevated temperature and pressure. The solution is then flashed under reduced process pressure or evaporated under constant or variant temperature, and with or without cooling, to produce PTA crystals that are not only similar to current commercial PTA in bulk density but also further purified to contain even less impurities.

Synergistic Effects

It was unexpectedly found in this invention that the solubilities of impurities remained to be high in many mixed solvents with properly selected co-solvent compositions after aromatic polycarboxylic acids were precipitated out of the solution. With one or more crystallization stages, the present invention is capable to process crude aromatic polycarboxylic acids with impurity content in a range of 0.0001 to 98%, preferably from about 0.5 to 30 wt %. This capability is considerably higher than the capacity of 0.5 to 1.0% of impurities that the current PTA purification processes can purify.

In addition, other impurities present in the crude aromatic polycarboxylic acids from processes other than catalytic liquid-phase oxidation process, such as DMT or NDC esterification process, can also be easily separated from the aromatic polycarboxylic acid. Therefore, this invention can be used to co-produce purified aromatic polycarboxylic acids from a new or existing aromatic polycarboxylate ester plant. For example, monomethyl terephthalate is one of the major impurity in the crude acid from DMT process, and its solubility was found to be close to the two major impurities of p-toluic acid and benzoic acid. This process can then be used to co-produce terephthalic acid from the oxidizer of a DMT plant, wherein the oxidizer effluent is filtered or by other means to obtain the solids containing crude terephthalic acid.

Furthermore, acids used as solvent in the oxidation reaction section may be entrained with or included in the crude aromatic polycarboxylic acid. In most of current processes these residual acids need to be separated prior to entering the purification section. Since the process of this instant invention has great tolerance of residual acids presented in the crude aromatic polycarboxylic acids, residual acid recovery process steps before purification section can thus be eliminated. The present invention is capable to process crude aromatic polycarboxylic acids having residual acid solvent contents ranging from about 0 to about 30.0 wt %, preferably from about 0 to about 15 wt %, and most preferably from about 0 to about 5 wt %, depending on the specific aromatic polycarboxylic acid to be purified, the selected mixed solvent, and purification process conditions.

The aromatic polycarboxylic acid product purity from the present invention can be significantly higher than that obtained from the currently existing processes. Under properly selected conditions as described hereinwith, the process is even capable to remove some impurities from crude aromatic polycarboxylic acids to undetectable levels by current HPLC, High Pressure Liquid Chromatography, analytical method. As illustrated in Example 1, pure terephthalic acid with undetectable level of benzoic acid and p-toluic acid and 8 ppm of 4-CBA in a single stage of crystallization had been achieved. After optimization of the process or adding one or more crystallization stages, it is possible to reach to the purity level where all of the three impurities cannot be detected by the current HPLC measuring method. Product purity from this invention can reach to about 99.99999% level. The ultra pure product can be used to develop new applications that are impossible with the current available product purity.

To meet polymer-grade PTA specification, current purification methods by hydrogenation or oxidation, allow total impurity level in crude terephthalic acid only up to 1 wt %, preferably 0.5 wt % to avoid overloading the purification section. To reduce impurity concentrations, either the oxidation reaction section producing crude aromatic polycarboxylic acid from starting materials is modified to run at higher severity, or additional process steps are added after the oxidation reaction step. Examples of such additional steps are secondary oxidation and reslurry in fresh acetic acid. However, since the purification process in this invention allows processing up to about 98 wt % total impurity in the crude aromatic polycarboxylic acid feed and can still meet the polymer grade specification, it relaxes requirements in the oxidation reaction section and imparts the following additional synergistic effects.

To [a] substitute the solvent used in the crude aromatic polycarboxylic acid producing oxidation reactor with less corrosive materials, such as benzoic acid, methyl benzoate, ethyl benzoate, and phenyl benzoate, [b] use less amount of oxidation promoters, [c] use different kind of promoters, [d] reduce the severity of operating condition by reducing reaction temperature to 100 to 175° C., [e] use a combination of the aforementioned [a] through [d] in order to use cheaper construction material, such as 316 SS, in the oxidation reactor or other parts of the process for lower capital investment.

To run the oxidation reaction producing the crude aromatic polycarboxylic acid at a lower severity to reduce combustion loss of feedstock and acid solvent and to recycle the un-reacted feedstock back to oxidation reaction vessel to increase the overall yield and production efficiency.

To process crude aromatic polycarboxylic acids from processes that are less efficient in producing high-purity product but cheaper in initial capital investment or operation cost. Examples are Henkel processes, $HNO_3$ oxidation of PX, the terephthalic acid or NDA from DMT or NDC process respectively, etc. Impurity contents obtained from such esterification processes may be as high as 30 wt %.

Further Descriptions

The purification processes in the instant invention are applicable to crude aromatic polycarboxylic acids having one, two, and three or more condensed rings with two or more carboxylic acid groups at any position of the ring or rings. The processes use two major solvents: N,X-monocyclic compound and alkylamine compound, and two co-solvents: water and alcohol. Five processes can be used to purified the crude acids. In consideration of previously described prior art (U.S. Pat. No. 5,344,969) that used alkylamine compound as major solvent; alcohol as co-solvent; processes similar to Process 3, 4, and 5 to purify crude aromatic polycarboxylic acids having two condensed rings and two carboxylic acid groups, the instant invention is applicable in four aspects that are summarized as follows:

The invented processes can be carried out with or without a purge of a non-oxidizing or inert gas. Such a gas is selected from the group of $N_2$, $CO_2$, CO, He, Ar, $H_2$, and mixtures thereof The crude aromatic polycarboxylic acid contains from about 0.000 wt % to about 98.0 wt % impurities, preferably from about 0.5 wt % to about 30 wt % or from about 0.000 wt % to about 0.1 wt %. It may also contain from about 0 wt % to about 30.0 wt % residual acid used and produced in producing the crude aromatic polycarboxylic acid. At least portions of the impurities present can be recycled.

A mixture of major solvent and co-solvent can be in one or multiple phases. All these purification processes can be used for 1 to 100 times, preferably for 1 to 3 times. In Process 1, 3, and 5, the amount of acid solvent used to precipitate said aromatic polycarboxylic acid, in molar ratio, is from about 0.01 to about 100 times of the crude aromatic polycarboxylic acid at a temperature range of −100 to 350 ° C. and the precipitation step is carried out in a period of 0 to 10 hours, more preferably from about 0.2 to about 10 times of the crude acid at a temperature range of 25 to 180° C. and carried out in a period of 0 to 2 hours. An aliphatic carboxylic acid having up to 15 carbon atoms, such as acetic acid, is preferred.

When Process 1 or Process 2 is used, the composition of said solvent is changed by removing lower-boiling components in the mixed solvent by one or a combination of the following methods: flashing under reduced process pressure, evaporating at constant or variant temperatures, distillation, adding a co-solvent. The preferred amount of solvent removed is from about 0.1 wt % to about 100 wt % of the original weight of the solvent used. The temperature range is between −100 and 350° C. and the pressure is in the range of 1 mm Hg to 760,000 mm Hg (1000 atmospheres) absolute. Preferred ranges are 25 to 180° C. and 25 mm Hg to 7,600 mm Hg (10 atmospheres) absolute, respectively.

When Processes 3, or 4 is used, the preferred temperature for dissolution is in the range from about −100 to about 350° C., preferably from about 80 to 170° C., and the preferred temperature to cooled to is in the range from about −100 to about 150° C., preferably from about 25 to about 100° C. When Process 5 is used, the preferred temperature to carry out the purification process is in the range from about −100 to about 350° C., most preferably from 25 to 180° C. Process 1 or 2 is preferred when co-solvent is used together with the major solvent.

The pre-treatment and/or post-treatment described above can be used in conjunction with all parts of this aspect of the invented process.

In the case of purifying terephthalic acid, dimethyl terephthalate (DMT) can be a co-product and the crude terephthalic acid is from downstream of an oxidizer in a DMT esterification process. In the cases of purifying naphthalene dicarboxylic acids, dimethyl naphthalene dicarboxylate is a co-product and the crude naphthalene dicarboxylic acid is from downstream of an oxidizer in a naphthalene dicarboxylic acid esterification process.

The crude aromatic polycarboxylic acid can be produced in an oxidation process using a less corrosive solvent selected from the group of benzoic acid, methyl benzoate, ethyl benzoate, phenyl benzoate and mixtures thereof. These processes are capable of producing an aromatic polycarboxylic acid of purity of 99.999 wt %, or 99.9999 wt % or as high as 99.99999 wt %. The crude aromatic polycarboxylic acid can be produced in an oxidation process operating at a temperature from about 100 to about 175° C., much lower than the prevalent commercial reaction temperatures wherein total impurity concentration is in the range from about 0.1 wt % to about 30 wt %. The oxidation reactor or vessel can be made of stainless steel materials.

Below are more detailed descriptions of the four aspects of the invented processes.

First Aspect

In this aspect, it involves a process for purifying a crude aromatic polycarboxylic acid having one or more condensed rings, which comprises the following steps: a) dissolving said crude aromatic polycarboxylic acid in a solvent comprising a major solvent or a mixture of a major solvent and one or more co-solvents, and wherein said co-solvent is selected from the group consisting of water, an acid solvent, an oxygen-containing solvent, and mixtures thereof wherein the proportion of said major solvent to said co-solvent is in the range of 0.1:99.9 to 99.9:0.1 by weight, and wherein said solvent is used in an amount from 0.1 to 100 times by weight the amount of said crude aromatic polycarboxylic acid; and b) conducting purification process; and c) filtering; to obtain a high purity aromatic polycarboxylic acid product having one or more condensed rings. Drying after filtering is a preferred embodiment of this invention.

Examples of aromatic polycarboxylic acids amenable to this process are terephthalic acid, isophthalic acid, orthophthalic acid, trimellitic acid, pyromellitic acids, 2,6-naphthalene dicarboxylic acid, 2,7-naphthalene dicarboxylic acid, 1,7-naphthalene dicarboxylic acid, 1,8-naphthalene dicarboxylic acid, 2,3,6-naphthalene tricarboxylic acid, and others.

Examples of preferred major solvent and co-solvent combinations are: a major solvent comprising an N,X-monocyclic compound, an alkylamine compound, or a mixture of the two compounds, a major solvent and a co-solvent comprising water, a major solvent and an acid solvent, a morpholine compound and water; an N,X-monocyclic compound and water, a major solvent and an oxygen-containing compound. Preferred alkylamine compound is triethylamine and triethanolamine. The most preferred mixed solvent is morpholine and a co-solvent comprising water.

All of the five purification processes as described above are applicable to this aspect of the invented process.

Second Aspect

Another aspect of this instant invention involves a process for purifying a crude aromatic polycarboxylic acid having one or three condensed rings, which comprises the following steps: a) dissolving said crude aromatic polycarboxylic acid in a solvent comprising a major solvent or a mixture of a major solvent and one or more co-solvents, wherein said co-solvent is selected from the group consisting of an alcohol, water, an acid solvent, an oxygen-containing solvent, and mixtures thereof, wherein the proportion of said major solvent to said co-solvent is in the range of 0.1:99.9 to 99.9:0.1 by weight, and wherein said solvent is used in an amount from 0.1 to 100 times by weight the amount of said crude aromatic polycarboxylic acid; and b) conducting purification process; and c) filtering; to obtain a high purity aromatic polycarboxylic acid product having one or three condensed rings. Drying after filtering is a preferred embodiment of this invention.

Examples of aromatic polycarboxylic acids amenable to this process are terephthalic acid, isophthalic acid, orthophthalic acid, trimellitic acid, pyromellitic acids, and others.

Some typical preferred major solvent and co-solvent combinations are: a major solvent comprising an N,X-monocyclic compound, an alkylamine compound, or a mixture of the two compounds, a major solvent and water, a major solvent and an alcohol, a major solvent and an acid solvent, a morpholine compound and water; an N,X-monocyclic and water, a major solvent and an oxygen-containing compound. Preferred alkylamine compound is triethylamine and triethanolamine. Co-solvent is preferably water, methanol, or ethanol. Water and methanol are the most preferred co-solvent.

All of the five purification processes as described above are applicable to this aspect of the invented process.

Third Aspect

Yet another aspect of this invention involves a process for purifying a crude aromatic polycarboxylic acid having two condensed rings, which comprises the following steps: a) dissolving said crude aromatic polycarboxylic acid in a solvent comprising an N,X-monocyclic compound or a mixture of an N,X-monocyclic compound and one or more co-solvents wherein said co-solvent is selected from the group consisting of an alcohol, water, an acid solvent, an oxygen-containing solvent, and mixtures thereof wherein the proportion of said major solvent to said co-solvent is in the range of 0.1:99.9 to 99.9:0.1 by weight, and wherein said solvent is used in an amount from 0.1 to 100 times by weight the amount of said crude aromatic polycarboxylic acid; and; b) conducting purification process to precipitate said aromatic polycarboxylic acid; and c) filtering; to obtain a high purity aromatic polycarboxylic acid product having two condensed rings. Drying after filtering is a preferred embodiment of this invention.

Examples of aromatic polycarboxylic acids amenable to this process are 2,6-naphthalene dicarboxylic acid, 2,7-naphthalene dicarboxylic acid, 1,7-naphthalene dicarboxylic acid, 1,8-naphthalene dicarboxylic acid, 2,3,6-tricarboxylic acid, and others.

N,X-monocyclic compound is the major solvent in this aspect. Some preferred combinations are: a major solvent and water, a major solvent and an alcohol, a major solvent and an acid solvent, a major solvent and an oxygen-containing compound. Preferred N,X-monocyclic compound is morpholine compound, and the most preferred is morpholine. Preferred co-solvent is water, methanol, or ethanol. The most preferred co-solvent is water and methanol.

All of the five purification processes as described above are applicable to this aspect of the invented process.

Fourth Aspect

A further aspect of this invention involves a process for purifying a crude aromatic polycarboxylic acid having two condensed rings, which comprises the following steps: a) dissolving said crude aromatic polycarboxylic acid in a solvent comprising an alkylamine compound or a mixture of an alkylamine compound and one or more co-solvents wherein said co-solvent is selected from the group consisting of an alcohol, water, acid solvent, oxygen-containing solvent, and mixtures thereof wherein the proportion of said major solvent to said co-solvent is in the range of 0.1:99.9 to 99.9:0.1 by weight, and wherein said solvent is used in an amount from 0.1 to 100 times by weight the amount of said crude aromatic polycarboxylic acid; b) conducting purification process to precipitate said aromatic polycarboxylic acid wherein the composition of said solvent is changed by removing a portion of said solvent; and c) filtering; to obtain a high purity aromatic polycarboxylic acid product having two condensed rings. Drying after filtering is a preferred embodiment of this invention.

Examples of aromatic polycarboxylic acids amenable to this process are 2,6-naphthalene dicarboxylic acid, 2,7-naphthalene dicarboxylic acid, 1,7-naphthalene dicarboxylic acid, 1,8-naphthalene dicarboxylic acid, 2,3,6-tricarboxylic acid, and others.

Alkylamine compound is the major solvent in this aspect. Some preferred combinations are: a major solvent and water, a major solvent and an alcohol, a major solvent and an acid solvent, a major solvent and an oxygen-containing compound. Preferred alkylamine compound is triethylamine and triethanolamine. Preferred co-solvent is water, methanol, or ethanol. The most preferred co-solvent is water and methanol.

Process 1 and Process 2 of the purification processes as described above are applicable to this aspect of the invented process.

The following examples are presented hereinafter to facilitate an understanding of the process of the present invention. They are presented for the purposes of illustration only and are not intended to limit the scope of the present invention.

EXAMPLE A (Prior Art, Comparative Example)

A sample of crude terephthalic acid (CTA) from a PTA manufacturer with the following levels of impurities was used in the experiment:

|  | 4-CBA | Benzoic Acid | p-Toluic Acid |
| --- | --- | --- | --- |
| PTA(ppmw) | 2436 | 1097 | 515 |

Where ppmw means parts per million by weight.

A CTA with similar composition was then subject to a conventional hydrogenation purification method as discussed in the prior art to give a PTA product with the following impurity level:

|  | 4-CBA | Benzoic Acid | p-Toluic Acid |
| --- | --- | --- | --- |
| PTA(ppmw) | 15 | 0 | 141 |

EXAMPLE B (Prior Art, Comparative Example)

Similar experiment as Example A is carried out with an oxidation purification process method as discussed in the prior art. The PTA product contained the following levels of impurities:

|  | 4-CBA | Benzoic Acid | p-Toluic Acid |
| --- | --- | --- | --- |
| PTA(ppmw) | 25 | 52 | 150 |

The impurity levels in the purified products represent typical commercially available polymer grade terephthalic acid. The following examples illustrate this instant invention.

EXAMPLE 1

A sample of 15 grams of CTA used in Example A was dissolved at room temperature into a solution containing 32 grams of morpholine and 30 grams of water. The temperature of this solution was raised to and maintained at 140° C., under atmospheric pressure, long enough to reduce the total solution volume by 19 c.c. The solution was then cooled to allow solids to precipitate. These precipitated solids were then filtered to separate from the mother liquor. The filter cake was subsequently washed with a morpholine and water mixture. The recovered solids were then reslurried in 27 grams of acetic acid, followed by filtration, rinse with water, and drying. A dried cake, 7.4 grams, of purified terephthalic acid was obtained. Analysis with HPLC showed the PTA contained.

|  | 4-CBA | Benzoic Acid | p-Toluic Acid |
| --- | --- | --- | --- |
| PTA(ppmw) | 8 | 0 | 0 |

EXAMPLE 2

An experiment similar to Example 1 was carried out with a mixed solvent containing a mixture of 50% H2O and 50% N-methyl morpholine at room temperature. Terephthalic acid has negligible solubility in either pure N-methyl morpholine or water alone. Its solubility in the mixed solvent in this experiment was found to be about 38 wt % at room temperature. This solution was treated with 50 wt % acetic acid in water to precipitate a crystalline terephthalic acid product of higher purity.

EXAMPLE 3

An experiment similar to Example 2 was carried out with methanol used to replace water as the co-solvent for N-methyl morpholine. Terephthalic acid solubility was found to be 30 wt % at 60° C. After dissolving CTA at 60° C., the solution was allowed to cool to room temperature, at which temperature terephthalic acid has a solubility of only 8 wt %. Terephthalic acid solids with improved purity were precipitated in the process.

EXAMPLE 4

An experiment similar to Experiment 2 is carried out with a mixed solvent containing 50 wt % triethylamine and 50 wt % water. At room temperature, terephthalic acid has negligible solubilities in either pure triethylamine or water. However, it was unexpectedly found that terephthalic acid is soluble in the mixture of triethylamine and water that contains significant portion of water. The solubility was found reaching about 28 wt % in the 50/50 mixture. The solubilities of benzoic acid, 4-CBA, and p-toluic acid were found to be around 155 wt %, 70 wt %, and 90 wt % in the 50/50 mixture respectively. From the above solubility data, terephthalic acid purity can be improved by first dissolving the crude terephthalic acid in a mixed solvent of 50% water and 50% triethylamine at room temperature. The water content is then reduced from 50 wt % to approximately 10 wt %. Terephthalic acid with improved purity can be obtained.

EXAMPLE 5

An experiment similar to Example 4 is carried out by replacing water with methanol as the co-solvent. The solubility was found reaching to about 48 wt % at room temperature in the solvent mixture which contains 50 wt % methanol. From the above solubility data, terephthalic acid purity can be improved by dissolving the crude terephthalic acid in a mixed solvent of 50 wt % methanol and 50 wt % triethylamine at room temperature. Most of the impurities are found to remain in solution when adequate amount of acid is added to the solution to precipitate out terephthalic acid solids. When a 50 wt % of aqueous acetic acid solution is added to the solution containing CTA, terephthalic acid solids with improved purity can be obtained by precipitation.

EXAMPLE 6

An experiment is carried out by dissolving CTA in pure N-methyl morpholine oxide at 80° C. The solubility of terephthalic acid at 80° C. was found to be 22 wt %. However, its solubility was found to decrease to about 1 wt % in a mixed solvent containing 75 wt % of water and 25 wt % N-methyl morpholine oxide at room temperature. Solubilities of other impurities were found to be significantly higher than the solubility of terephthalic acid under similar conditions. The CTA containing solution is cooled down to room temperature and an amount of water equal to three times the weight of N-methyl morpholine oxide is added. Terephthalic acid of improved purity is precipitated out of the solution.

EXAMPLE 7

An experiment similar to Example 2 is carried out to purify 2,6-naphthalene dicarboxylic acid (2,6-NDA). At room temperature 2,6-NDA has negligible solubilities in either pure morpholine or water. However, it was unexpectedly found that the solubility of 2,6-NDC increased to about 12 wt % in a solvent mixture that contained 40 wt % water and 60 wt % morpholine. The solubility of 1,2,4-benenetricarboxylic acid, a known impurity in crude 2,6-NDA, was found to be much higher at about 45 wt % at 40 wt % of H2O. Solubilities of other impurities in crude 2,6-NDA are expected to be significantly higher than the solubility of 2,6-NDA.

Crude 2,6-NDA is dissolved in a mixed solvent of 40 wt % water and 60 wt % morpholine at room temperature. When a 40 wt % acetic acid in water is added to the solution containing crude 2,6-NDA, 2,6-naphthalene polycarboxylic solids with improved purity are precipitated out of the solution.

EXAMPLE 8

An experiment similar to Example 2 is carried out to purify isophthalic acid. At room temperature a crude isophthalic acid sample is dissolved in a mixed solvent containing of 50 wt % water and 50 wt % morpholine. At room temperature, isophthalic acid has negligible solubilities in either pure morpholine or water. However, in this mixed solvent containing of 50 wt % water and 50 wt % morpholine, the solubility of isophthalic acid was unexpectedly found to be about 53 wt % at room temperature. At the same time, the solubilities of m-toluic acid and benzoic acid, known impurities in crude isophthalic acid, were found to be 50 to 105 wt % in the same mixed solvent. To this solution containing crude isophthalic acid is added acetic acid. Solids of isophthalic acid with improved purity are precipitated out of the solution.

What is claimed is:

1. A method for purifing a crude aromatic polycarboxylic acid having one or more condensed rings, or a derivative thereof, which comprises:
    a) dissolving a salt formed by said crude aromatic polycarboxylic acid, or said derivative, and a morpholine compound in a co-solvent;
    b) removing impurities from the salt using one or more processes selected from a group consisting of pretreatment, precipitating by changing composition, precipitating by cooling, and precipitating by adding an acid solvent; and
    c) recovering a purified aromatic polycarboxylic acid, or a purified derivative thereof, from the salt using a process selected from a group consisting of adding an acid solvent to the salt and thermally decomposing the salt.

2. The method as claimed in claim 1, wherein said co-solvent is water.

3. The method as claimed in claim 1, wherein said co-solvent is an alcohol.

4. The method as claimed in claim 1, wherein the proportion of said morpholine compound to said co-solvent is in a range of 0.1:99.9 to 99.9:0.1 by weight.

5. The method as claimed in claim 1, wherein said morpholine compound is used in an amount from 0.1 to 100 times by weight of the amount of said crude aromatic polycarboxylic acid, or said derivative.

6. The method as claimed in claim 1, wherein said precipitating by changing composition removes 0.1 to 100 weight percent of the total amount of solvents used to dissolve said crude aromatic polycarboxylic acid, or said derivative.

7. The method as claimed in claim 1, wherein said dissolving occurs at a temperature in the range of −100 to 350° C. and the solution is cooled to a range of −100 to 150° C.

8. The method as claimed in claim 1, wherein said dissolving occurs at a temperature in the range of 30 to 180° C. and the solution is cooled to a range of 25 to 100° C.

9. The method as claimed in claim 1, wherein said aromatic polycarboxylic acid is terephthalic acid.

10. The method as claimed in claim 1, wherein said aromatic polycarboxylic acid is isophthalic acid.

11. The method as claimed in claim 1, wherein said aromatic polycarboxylic acid is a naphthalene dicarboxylic acid.

12. The method as claimed in claim 1, wherein said acid solvent is used in an amount from 0.2 to 10 times by mole to the amount of said crude aromatic polycarboxylic acid, or said derivative.

13. The method as claimed in claim 1, wherein said morpholine compound is morpholine.

* * * * *